United States Patent [19]
Pauley et al.

[11] Patent Number: 5,238,840
[45] Date of Patent: Aug. 24, 1993

[54] IMMORTAL HUMAN MAMMARY EPITHELIAL CELL SUBLINES

[75] Inventors: Robert J. Pauley, Farmington; Terry J. Paine, Detroit; Herbert D. Soule, Dearborn, all of Mich.

[73] Assignee: Michigan Cancer Foundation, Detroit, Mich.

[21] Appl. No.: 727,519

[22] Filed: Jul. 9, 1991

[51] Int. Cl.$^5$ .......................... C12N 5/00; C12N 5/08
[52] U.S. Cl. ................................ 435/240.2; 435/240.1
[58] Field of Search ........................... 435/240.1, 240.2

[56] References Cited

U.S. PATENT DOCUMENTS

| | | | |
|---|---|---|---|
| 4,423,145 | 12/1983 | Stampfer et al. | 435/240.23 |
| 4,808,532 | 2/1989 | Stampfer | 435/240.2 |
| 5,026,637 | 6/1991 | Soule et al. | 435/240.2 |

OTHER PUBLICATIONS

Bano et al, J. of Biological Chemistry, 265(4) pp. 1874–1880 (1990).
Trask et al, Proc. Natl. Acad. Sci. USA, 87, pp. 2319–2323, Mar. 1990.
Zajchowski et al, Proc. Natl. Acad. Sci. USA, 87, pp. 2314–2318, Mar. 1990.
Eldridge et al, Cancer Research, 49, pp. 4326–4331, Aug. 1, 1989.
*In Vitro*, vol. 20, No. 8 (Aug. 1984).
*In Vitro Cellular and Developmental Biology*, vol. 22, No. 1 (Jan. 1986).
Abstract 1780, Proc. AACR, vol. 29, 448 (Mar. 1988).

*Primary Examiner*—Douglas W. Robinson
*Assistant Examiner*—Susan M. Weber
*Attorney, Agent, or Firm*—Dykema Gossett

[57] ABSTRACT

Two immortalized human mammary epithelial cell sublines are provided. The sublines do not undergo terminal differentiation and senescence upon exposure to high calcium concentrations. The sublines exhibit positive reactivity with milk-fat globule membrane and cytokeratin anti-sera and are non-tumorigenic in athymic mice. The sublines are useful in evaluating the capacity of preselected agents to bring about a change in epithelial cell growth and in the production of proteins.

4 Claims, 2 Drawing Sheets

IMMORTAL HUMAN MAMMARY EPITHELIAL CELL SUBLINES

The discovery of the present invention was supported by NIH Grants CA22453 and RR05529 and an institutional grant from the Detroit United Way.

FIELD OF THE INVENTION

The present invention relates generally to human epithelial cells. More specifically, the present invention provides a new immortalized human mammary epithelial cell line and methods of using the novel cells in research and industry.

BACKGROUND OF THE INVENTION

The principle of limited cell division potential of somatic cells in vitro is well established. In a number of fields, researchers utilize somatic cell cultures from normal tissues in order to study the mechanisms underlying intercellular interaction and cellular response to various stimuli. These include such diverse pursuits as evaluating the carcinogenicity of selected agents, determining the activities of various hormones, monitoring the reactions of chemotherapeutic agents, and in general studying the metabolic characteristics of a given cell type. However, the phenomenon of limited cell division of normal cells complicates these efforts and often prevents long-term evaluation of cell sensitivity and induced expression.

More specifically, the study by oncologists of neoplastic transformation of epithelial cells has been severely limited by the relatively limited in vitro population longevity. This has led to the use of human fibroblast cultures which have greater in vitro longevity as the accepted model for transformation studies. However, it has been noted that the analogy drawn between these two distinct cell-types is tenuous at best and that the lack of a true long-term epithelial model has hindered cancer research. This is despite the fact that neoplasms of epithelial origin are the most prevalent type of cancer in humans.

In particular, it is known that conventional human mammary epithelial cells generally have at most a limited cell division potential (generally about 13 doublings). In "A Simplified Method For Passage and Long-Term Growth of Human Mammary Epithelial Cells," *In Vitro Cellular and Developmental Biology*, vol. 22, No. 1, January, 1986, which is incorporated herein by reference, a method of culturing non-neoplastic human mammary epithelial cells which extends the population longevity of these cells beyond the previously reported limit of 13 doublings to more than 50 generations was reported. Longevity was achieved by reducing the Ca++ concentration of the media which in turn reduced an inhibition effect in which glucocorticoids induced terminal differentiation. A significant observation which was made in these studies was that conventional human mammary epithelial cells in culture media greater than 0.06 mM ionic calcium underwent terminal differentiation after only three or four passages from primary culture.

More recently, in U.S. Pat. No. 5,026,637 filed Feb. 28, 1989, an immortal human mammary epithelial cell line, which contained sublines designated MCF-10A and MCF-10F, was described. This earlier patent application, which is assigned to the same assignee as the present application, is hereby incorporated by reference. The cell sublines MCF-10A and MCF-10F demonstrated unlimited cell division potential and produced mammary epithelial cell proteins. These cell sublines were capable of subsisting in a high-calcium media without undergoing calcium-induced cellular senescence. Both earlier cell sublines MCF-10A and MCF-10F were non-tumorigenic in athymic mice and demonstrated a characteristic response to treatment with insulin, epidermal growth factor, and cortisol.

A new immortal human mammary epithelial cell line, described herein, has been developed. This cell line (designated MCF-10-2) was derived from the same ultimate tissue sample as the previously reported cell sublines MCF-10A and MCF-10F. Cell line MCF-10-2 consists of two sublines, designated MCF-10-2A and MCF-10-2F.

It is desirable to provide several genetically different, non-neoplastic epithelial cell lines which could be cultured indefinitely to permit long-term evaluation of suspected reactive agents. It would also be desirable to provide such cell lines which produce a complement of proteins characteristic of normal human breast epithelial cells. It would be further desirable to provide a method by which epithelial cell sensitivity to suspected reactive agents and cellular expression thereby induced could be studied on a long-term basis. Different interactions of the reactive agents and cellular expression in the various cell lines and sublines may prove especially useful. The present invention satisfies these goals by providing a new non-neoplastic human mammary epithelial cell line for use in cell culture studies.

SUMMARY OF THE INVENTION

In accordance with the present invention there is provided in one aspect a cell line of immortal non-neoplastic human mammary cells, the cell line being designated MCF-10-2, which have unlimited cell division potential and which produce mammary epithelial cell proteins. Cell line MCF-10-2 consists of two sublines, designated as MCF-10-2A and MCF-10-2F. The novel cell sublines of the present invention are provided as biologically pure cultures and are capable of subsisting in a high-calcium media without undergoing calcium-induced cellular senescence. MCF-10-2A and MCF-10-2F are non-tumorigenic in athymic mice.

In still another aspect, the present invention provides a method for testing the long-term biological activity of a preselected agent on epithelial cell growth in vitro which comprises the steps of exposing a culture of immortalized human mammary epithelial cells, as provided by the present invention under the designations MCF-10-2A and MCF-10-2F, to a preselected agent and monitoring cellular sensitivity and/or induced altered cellular expression.

Hence, it is an object of the present invention to provide two immortal sublines of a non-neoplastic human mammary epithelial cell line to be used as models in epithelial cell studies. Combined with the sublines described in the previous patent application described above and Applicant's copending application U.S. Ser. No. 07/727,519, filed Jul. 9, 1991 entitled "Immortal Human Mammary Epithelial Cell Line", six different sublines of non-neoplastic human mammary epithelial cells are now available for such modeling. This copending application, which is assigned to the same assignee as the present invention and is hereby incorporated by reference, describes a new immortal epithelial cell line with two sublines, which are designated MCF-12A and MCF-12F.

It is a further object of the present invention to provide a method by which the activities of preselected agents on epithelial cells can be observed over extended periods.

These and other objects and advantages of the present invention will become apparent through the following description of the preferred embodiments of the invention and with reference to the drawings in which:

DESCRIPTION OF THE PREFERRED EMBODIMENTS

The present invention provides two sublines of a non-neoplastic immortal human breast epithelial cell line. This cell line, designated MCF-10-2, consists of two sublines designated as MCF-10-2A and MCF-10-2F. Cultures of MCF-10-2A and MCF-10-2F were deposited on Jun. 20, 1991, with the American Type Culture Collection (ATCC) at 12301 Parkland Drive in Rockville, Md., 20852 under the Budapest Treaty on the International Recognition of the Deposit of Microorganisms for the Purposes of Patent Procedures. The following ATCC Registration Numbers have been assigned: for subline MCF-10-2A, Registration No. ATCC CRL 10781; and for subline MCF-10-2F, Registration No. ATCC CRL 10780.

The immortal cell line of the present invention comprises human mammary epithelial cell sublines that are characterized by unlimited (immortal) cell division potential. The novel cell sublines of the present invention are resistant to high-calcium induced senescence which is typical of most prior art human mammary epithelial cells. MCF-10-2-A and MCF-10-2F express cytokeratins, milk-fat globule antigens (or polymorphic epithelial mucin) and other conventional mammary epithelial markers. These sublines are growth-responsive to insulin, epidermal growth factor, cholera enterotoxin, and cortisol. The novel sublines of the present invention are non-tumorigenic in athymic mice. These sublines also demonstrate dome formation in confluent cultures characteristic of epithelial cells. The sublines MCF-10-2A and MCF-10-2F appear to be immortal with retention of many characteristics of normal human breast epithelium and its conventional phenotypes.

MCF-10-2A and MCF-10-2F were produced by in vitro mutation. A causative, i.e. mutagenic, agent has not been identified, and thus the mutation shall be referred to herein as "spontaneous." In order to more fully understand the Applicants' novel cell line, the protocols utilized in discovery of the present invention will now be fully explained for the MCF-10-2 cell line.

Figure 1:
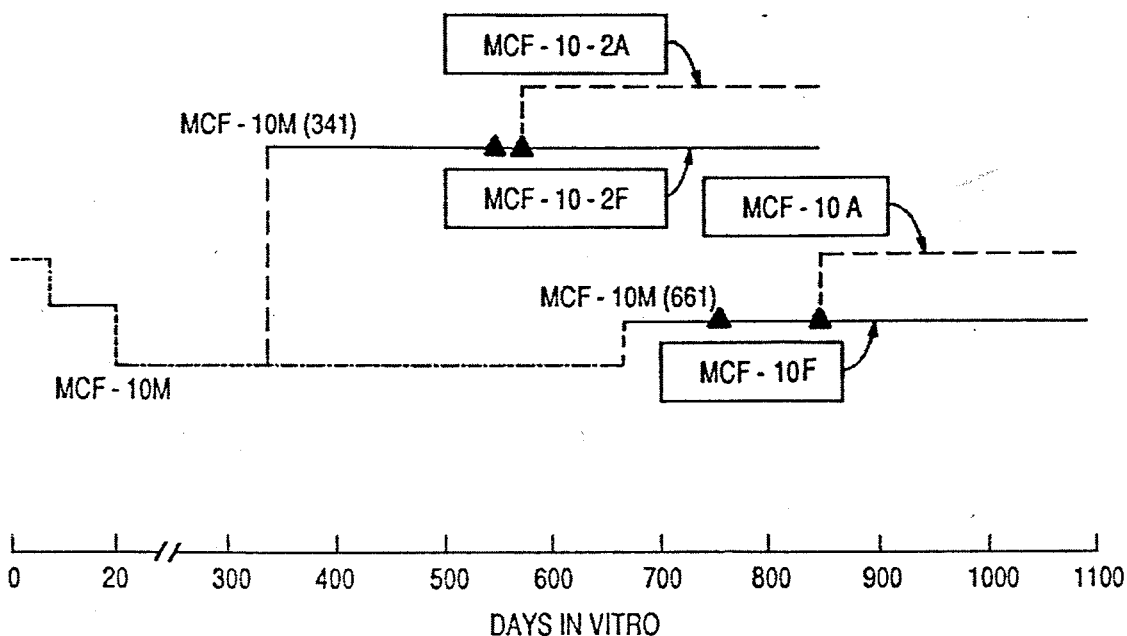
FIG. 1 is a flowchart illustrating the origin of the novel epithelial cell sublines MCF-10-2A and MCF-10-2F of the present invention and their relationship with the cell sublines MCF-10A and MCF-10F of U.S. Pat. No. 5,026,637.

Except as noted below, the procedures used were essentially the same as used in preparing MCF-10A and MCF-10F sublines as described in U.S. Pat. No. 5,026,637. FIG. 1 shows the relationship between sublines MCF-10A and sublines MCF-10F and sublines MCF-10-2A and MCF-10-2F. Tissue samples were obtained from a subcutaneous mastectomy. Cell sublines MCF-10A, MCF-10F, MCF-10-2A, and MCF-10-2F were all derived from this same tissue sample. The samples were observed for the presence of normally dense stroma and parenchyma, and then minced to fragments using a scalpel. These fragments were then further divided into cells and cell aggregates or organoids by treatment with collagenase and hyaluronidase using the procedures set forth in "Growth of Normal Human Mammary Cells In Culture," *In Vitro*, 615:415–425 (1980), which is incorporated herein by reference. Ten micrograms/ml insulin and 1.4 mM cortisol were included, with 10% serum in the digestion mixtures as detailed in "Renewal Inhibition of Human Mammary Epithelial Cell Growth in Vitro: Cortisol and the Recruitment Cells to Terminal Differentiation," *J. Cell Physiol.*, 116:385–396 (1983), which is incorporated herein by reference.

The resultant disassociated epithelium was then plated in primary culture as fully described in the immediately foregoing reference. The diploid mortal culture is designated MCF-10M in FIG. 1. Cell number was estimated from packed cell volumes. Primary cultures were generally cultured in 75 sq. cm (T-75) flasks. Succeeding cultures were plated in T-25 flasks, T-75 flasks, or 24-well plates. Mortal cells were subcultivated by passing free-floating cells. Cell viability was determined by the trypan blue exclusion test using a hemocytometer. Cell number and viability of the seed flasks were determined by performing a cell count when the nutrients were replenished. The number of doublings that occurred during the extended time periods in culture was calculated by determining total cell number released from a constant cell number that remained attached in confluent cultures.

During these experiments, Applicants were able to significantly extend the population longevity of epithelial cells without the continuous use of high calcium concentrations or enzymatic transfers as is more fully disclosed in "A Simplified Method For Passage and Long-Term Growth of Human Mammary Epithelial Cells," *In Vitro*, Vol. 22, No. 1 (January 1986). By continuing these cultures, the two immortalized eptihelial cell sublines MCF-10A and MCF-10F of patent application Ser. No. 07/317,610 and the two immortalized epithelial cell sublines MCF-10-2A and MCF-10-2F of the present invention were produced. All four sublines were derived from the diploid mortal culture MCF-10M which was cultured in serum-free medium with a low (0.04 mM) $Ca^{++}$ concentration. MCF-10M began to show a minimal increase in cell numbers at 341 days in vitro. Aliquots of the cell culture at 341 days were taken and cryopreserved (sample designated as MCF-10M[341] in FIG. 1).

As indicated in FIG. 1, the remainder of the culture (i.e. the portion not cryopreserved) was allowed to continue culturing in complete medium with a 0.04 mM $Ca^{++}$ level. This continuing culture ultimately gave rise to immortal sublines MCF-10A and MCF-10F which are fully described in U.S. Pat. No. 5,026,637.

The cryopreserved sample (MCF-10M[341]) was reactivated after 1459 days storage at −72° C. The reactivation medium was a low calcium (ca. 0.04 mM $Ca^{++}$) containing 5% chelexed (divalent ion free) equine serum. After about 560 days in vitro, the cells were found to have mutated whereby they had ceased to undergo calcium induced senescence. This immortal cell line in the low calcium, serum-containing medium is designated MCF-10-2F cells were plated in 1.05 mM $Ca^{++}$ with 5% equine serum and transferred serially with trypsin-versene. This immoral cell line was designated MCF-10-2A (see FIG. 1). At the time of filing U.S. Pat. No. 5,026,637 (Feb. 28, 1989), cryopreserved sample MCF-10M[341] remained frozen. As of Jun. 1, 1991, cell line MCF-10-2 has been maintained in a conventional calcium concentration (1.50 mM) medium for 442 days. The number of doublings that occurred was calculated by counting cells plated (F subline) or attached at day one (A subline) and cell number at transfer.

The culture media employed in these above-described studies will now be generally described. A 1:1 ratio of Dulbecco and Ham's F12 nutrients in admixture was utilized as the medium and was prepared de novo from the constituent compounds, using vitamins and amino acids obtained from Sigma Chemical Company. A basal salt solution was prepared without $CaCl_2$. Nutrients and salts were adjusted to a pH of 7.2 using HCl and NaOH and sterilized by filtration with 0.22 micrometer filters. Sterile $CaCl_2$ was added from 500 mM or 28.5 mM stock solutions to obtain 1.05 or 0.04 mM $Ca^{++}$, respectively. Divalent cations were removed from the serum using Chelex 100 (sodium form) obtained from Bio-Rad Laboratories pursuant to the method set forth in "Improved Methods for Reducing Calcium and Magnesium Concentration in Tissue Culture Medium: Application to Studies of Lymphoblast Proliferation In Vitro," *In Vitro*, 11:354–360 (1975), which is incorporated herein by reference. Initially, the level of calcium in the solutions was monitored by flame photometry. The serum was sterilized by filtration with a 0.45 micrometer filter and maintained at −20° C. until use. Penicillin (100 U/ml), streptomycin (100 micrograms/ml), amphotericin B (0.25 micrograms/ml), cholera enterotoxin (100 ng/ml), and epidermal growth factor (20 ng/ml) were used to supplement the media, as was 5% horse serum. Insulin (10 micrograms/ml) and cortisol ($1.4 \times 10^{-6}$M) were also routinely included in the media. Powdered calcium-free media (Gibco, formula no. 90-5212 EG) can be employed instead of the individual ingredients of Dulbecco and Hamm's F-12 media.

As used herein, the term "immortal" or "immortalized" shall mean that, based upon current observations, these cells, under the culture conditions described herein, have shown no tendency to undergo terminal differentiation of cell senescence, but rather retain the capacity to divide indefinitely. By "non-neoplastic," it is meant that the novel cell lines of the present invention demonstrate no indicia characteristic of neoplastic cells other than immortality and are non-tumorigenic when injected in athymic mice.

The preferred culture medium for MCF-10-2F is a medium consisting of 95% Dulbecco and Ham's F-12 (1:1 ration) nutrients and 5% equine serum with added epidermal growth factor (20 ng/ml), bovine insulin (10 mg/ml), cholera enterotoxin (100 ng/ml) and cortisol (1.4 nM), penicillin (100 units/ml), streptomycin (100 mg/ml), and amphotericin B (0.25 mg/ml) where the divalent ions were removed from equine serum with Chelex 100, the Dulbecco and Ham's F-12 nutrients were prepared without $CaCl_2$, and $Ca^{++}$ was added to obtain a 0.04 mM concentration. The preferred culture medium for MCF-10-2A was prepared in the same manner as the preferred MCF-10-2F medium except that the divalent ions were not removed from the equine serum and the $Ca^{++}$ was increased to a 1.05 mM concentration. MCF-10-2A is preferably grown as monolayers, transferred 1:25 weekly. MCF-10-2F is preferably grown as monolayers which yield free-floating cells and transferred 1:4 weekly with free-floating cells.

The protocol used to prepare the media used in the initial cultures of the tissue sample which gave rise to the MCF-10-2 cell line is described in detail in U.S. Pat. No. 5,026,637 and, therefore, need not be repeated here.

Referring now to FIG. 1 of the drawings, a flowchart is provided which illustrates the procedure by which the novel cell line MCF-10-2 of the present invention was prepared. FIG. 1 also illustrates the relationship of the novel cell line MCF-10-2 of the present invention with cell line MCF-10 of U.S. Pat. No. 5,026,637. The symbols used in FIG. 1 are interpreted as follows: Dashed (---) vertical lines indicate a change in the culture medium; dashed and dotted (-.-.) horizontal lines indicate a low calcium (0–0.6 mM $Ca^{++}$), fetuin/transferrin -supplemented 1:1 Dulbecco and Ham's F12 medium which is serum-free; solid () horizontal lines indicate a low calcium (0.04–0.06 mM $Ca^{++}$(, chelexed serum-supplemented 1:1 Dulbecco and Ham's F12 medium; dashed (---) horizontal line indicate a conventional calcium (ca. 1.05 mM $Ca^{++}$), serum-supplemented 1:1 Dulbecco and Ham's F12 medium; and solid triangles indicate the establishment of the respective immortal cell sublines indicated in boxes. Mortal breast epithelial cell with a finite life span (MCF-10M) were used as the starting culture. After 341 days in vitro an aliquot of the mortal cells was frozen (MCF-10M[341]). The MCF-10M cells were mortal at the time of their cyropreservation. Upon reactivation in a low calcium, serum-containing medium these cells became immortal at around 557 days in vitro (MCF-10-2F). Subline MCF-10-2A was derived from MCF-10-2F cells grown in a conventional calcium, serum-containing medium and transferred serially with trypsin-EDTA. Sublines MCF-10A and MCF-10F were derived from continuously cultivated mortal MCF-10M cells via mortal MCF-10M[661] cells as described in U.S. Pat. No. 5.026,637.

As stated, MCF-10-2A and MCF-10-2F are substantially normal, but immortalized, human mammary epithelial cell lines as determined by the following criteria: non-tumorigenieity in nude mice; presence of milk-fat globule membrane antigens; positive reactivity with cytokeratin antiserum; three-dimensional growth in collagen; growth control by hormones and growth factors; and dome formation in confluent cultures (1.05 mM $Ca^{++}$).

Figure 2:
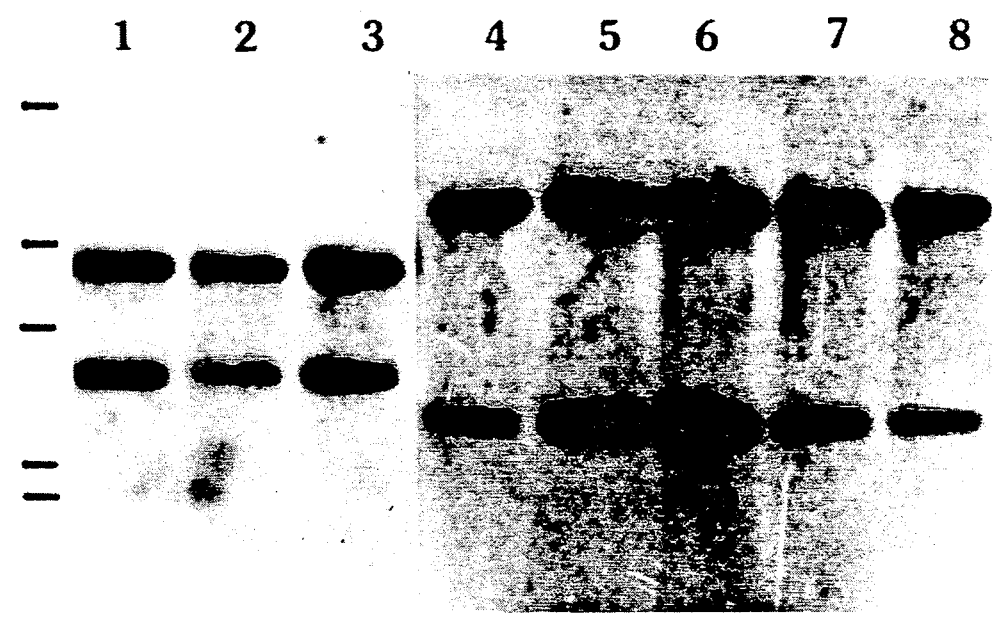
FIG. 2 is the DNA fingerprint of various immortal MCF-10-2A and MCF-10-2F cell cultures of this invention. Also included are the DNA fingerprints of precursor (mortal) cell cultures and the immortal MCF-10A and MCF-10F cultures as well as immortal MCF-12A and MCF-12F cell cultures of out copending application for comparison purposes.

DNA fingerprinting of the cell lines of the present invention demonstrate that the MCF-10-2 cell line is a distinct continuous human cell line that was not contaminated with human breast tumor cell lines maintained in Applicant's laboratory including the MCF-12 cell line described in Applicants' copending application. The DNA fingerprints of cell lines MCF-10, MCF-10-2 are shown in FIG. 2. (Cell lines MCF-10 and MCF-12 are shown for comparison purposes.) The cell line DNA's were analyzed for the highly polymorphic human MUC1 locus which has a frequency of heterozygosity in HinfI digests of approximately 0.80 in the 156 chromosomes examined. HinfI digest of 2 mg of DNA were size fractionated, hybridized with the pmuc10 probe, and sutoradiographed. The migration of lambda-HindIII size standards form 9.6 to 2.0 kb is indicated on the left-hand side of FIG. 2. The lanes and cell line DNA (with days of in vitro cultivation specified in parenthesis) in FIG. 2 are as follows: lane 1—MCF-12M (39days); lane 2—MCF-12A (1893 days); lane 3—MCF-12F (1908 days); lane 4—MCF-10M (395 days); lane 5—MCF-10A (1702 days); lane 6—MCF-10F (1852 days); lane 7—MCF-10-2A (854 days); and lane 8—MCF-10-2F (852 days). Mortal cell line MCF-10M is the precursor of immortal cell sublines MCF-10A and MCF-10F, which are described in more detail in patent application Ser. No. 07/317,610, and sublines MCF-10-2A and MCF-10-2F of the present invention. Mortal cell line MCF-12M is the precursor of immortal cell sublines MCF-12A and MCF-12F of Applicants' copending application. From this data it is concluded that the MCF-10, MCF-10-2, and MCF-12 cell lines are human, continuous cell lines; that MCF-10 and MCF-10-2 cell lines are of the same lineage; and that the MCF-12 cell line is of different lineage from the MCF-10 and MCF-10-2 cell lines.

Samples of MCF-10-2A cells injected into nude mice (5 week old athymic specimens) did not result in the formation of progressively growing tumors. Innoculum (ca. $10-15 \times 10^6$ cells) initially formed a mass ( the largest averaging about 4.8 to 5.5 mm one week after injection) which gradually decreased in size until, by the fifth week, no mass was palpable or visible. The initial mass contained cells which organized as duct-like structures and had non-malignant cytologic features. Based on these observations, the MCF-10-2 immortal cell line does not appear to be tumorigenic.

Figure 3:
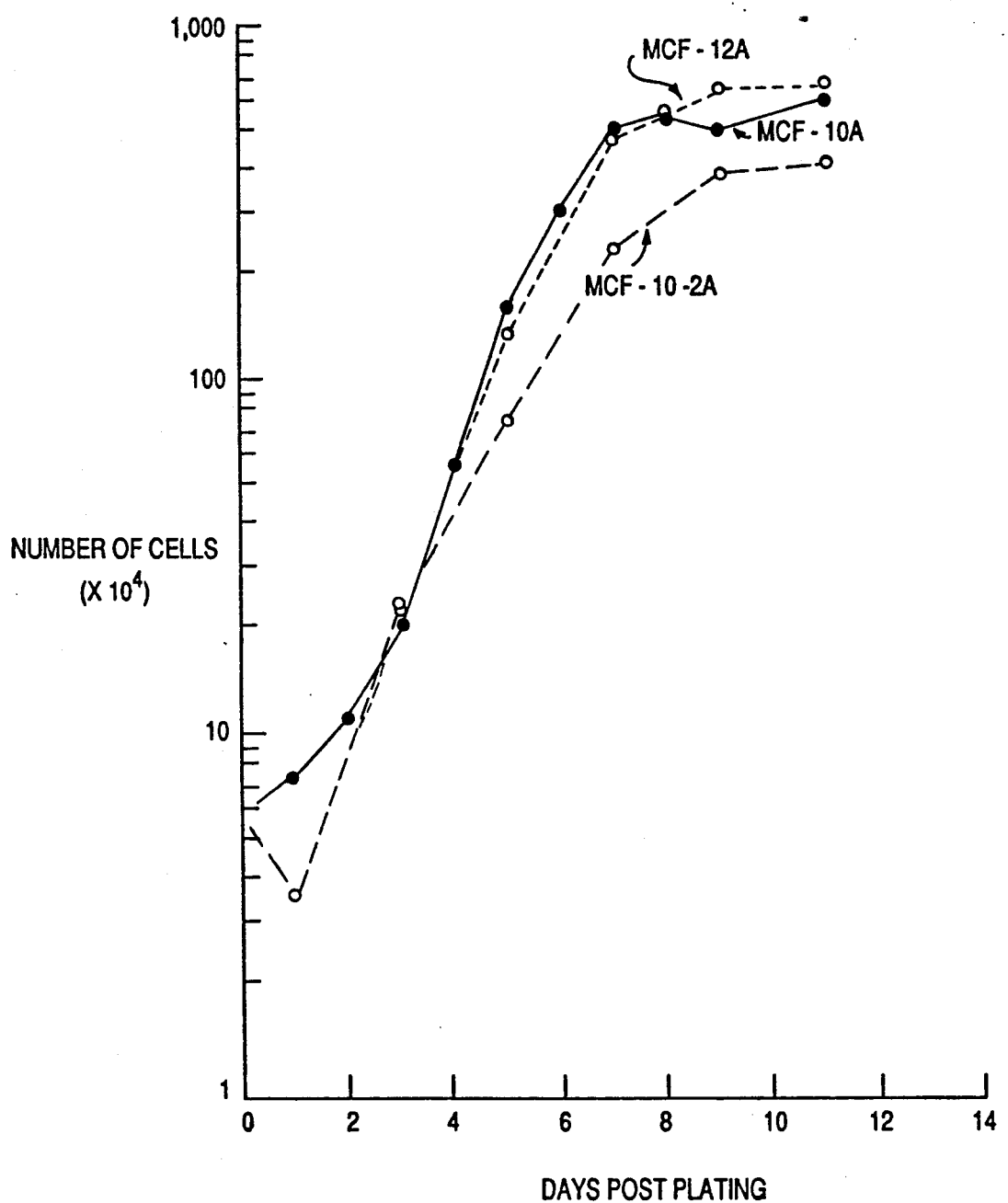
FIG. 3 shows the growth curve of immortal MCF-10-2A cell culture of the present invention. The growth curves of immortal MCF-10A cell culture and immortal MCF-12A cell culture of our copending application are shown for comparison purposes.

Growth curves for the immortal cell lines MCF-10A (solid line), MCF-10-2A (dashed line), and MCF-12A (dotted line) are shown in FIG. 3. (Growth curves for MCF-10A and MCF-12A are included for comparison purposes.) In this Figure, the number of cells on a logarithmic scale is plotted against time in days. For MCF-10A, MCF-10-2A, and MCF-12A, the days in vitro at the initiation of the growth curves were 2172, 896, and 1906 days, respectively; and the passage numbers were 166, 77, and 32, respectively. Cells were plated at $6 \times 10^4$ cells per $T_{25}$ flask. The medium was changed on days 1, 3, 5, 7, and 9. Cell counts were determined with a hemocytometer following cell removal with trypsin-EDTA. Each measured point is the mean of three determinations; the standard deviation was less than 7 percent.

Based on the growth curves of FIG. 3, doubling times and saturation densities were determined for the three immortal cell lines. Doubling times were 19.0, 19.9, and 21.4 ours with total number of doublings at day 11 of 7.2, 6.2, and 6.7 for MCF-12A, MCF-10A, and MCF-10-2A, respectively. The saturation densities of MCF-12A and MCF-10A were essentially the same (ca. $2.6 \times 10^4$ cells/cm$^2$) and about 1.5 times greater than that of MCF-10-2A. The lower saturation density of MCF-10-2A is due to its larger cell size.

Two morphological cell types are apparent in the monolayers of breast cultures grown in normal calcium level (ca. 1.05 mM) medium: (1) large cells which have abundant cytoplasm, are irregular in shape, often vacuolated, and appear to be differentiating and senescing; and (2) small cells which are more uniform in shape, non-vacuolated, and form colonies. MCF-10-2A, which has been in vitro the shortest time and which was immortalized at a relatively early time, shows a mixed population of large and small cells. MCF-10A and MCF-12F show a more uniform small cell morphology. This may suggest that the process of immortalization either occurred in, or involved, the selection for the small cell phenotype. Domes are observed infrequently in MCF-10-2A and only in post confluent monolayers. Domes are observed in MCF-10A and MCF-12A in areas of localized monolayers in pre-confluent cultures (day 6).

The MCF-10-2 cell line of the present invention was cytogenetically characterized using standard procedures. A culture of MCF-10A was harvested 21 days after the subline was established. The modal chromosome number was 42 with a spread from 40–43 chromosomes per cell. Each cell has one or two dmin pairs. Both numerical and structural aberrations mark the clonal population. A #13, #20, #22, and both members of the #18 pair were routine lost. Translocations involving shromosomes 6, 8, and 21 resulted in loss of 6p- and multiple copies of 8q. Deletions of 11p and both 9p were noted. Small non-uniform meta centric chromosomes involving translocations of some of the smallest missing or aberrant chromosomes (19, 21, and 22) were present in less that half the cells. The cytogenetic characterization of MCF-10-2A is summarized in Table 1 which follows:

TABLE 1

| Chromosomes Number | MCF-10-2A 40–43 |
|---|---|
| X | 2 |
| 1 | 2 |
| 7 | 2 |
| 8 | 2 |
| 9 | 2 |
| 10 | 2 |
| 11 | 2 |
| 12 | 2 |
| 13 | 1 |
| 18 | 0 |
| 20 | 1 |
| 22 | 1 |
| Double minutes | 2–4 |
| Markers | t(6;8)(6q;8p) |
|  | 8p-(p11.2) |
|  | t(8;21)(8q;21q) |
|  | two 9p-(p22) |
|  | 11p-(p15.1) |

The expression of various cytokeratins by the immortal cell line MCF-10-2 of the present invention, the immortal cell lines of U.S. Pat. No. 5,026,637 and the immortal cell line MCF-12 of Applicants' copending application were examined using the 2D gel western blot technique. Blots were prepared from each cell culture and reacted with anti-cytokeratin antibodies AE1 and AE3 which recognize all acidic and most basic cytokeratins, respectively, and with CK5 and K19.1 which are specific for cytokeratins 18 and 19, respectively. The three immortal cell lines showed similar luminal profile (cytokeratins 7,8,18, and 19) except for the variable expression of cytokeratin 19 which was lost in the MCF-10 and MCF-12 cell lines but retained in the MCF-10-2 cell line.

Immunoperoxidase staining with a monospecific antibody directed against cytokeratin 19 (antibody K19.1) was performed to determine if expression of this antigen could be correlated to the large or small cell type. The staining results are presented in the following Table 2.

TABLE 2

| Cell Culture | Days in vitro | Cytokeratin 19 Expression | |
|---|---|---|---|
| | | Large Cells | Small Cells |
| MCF-10M[661] | N.D. | | |
| MCF-10A | 1708 | − | −* |
| | 1933 | − | −* |
| MCF-10F | 843 | + | ± |
| | 2066 | − | −* |
| MCF-10M[341] | 440 | ++ | ++ |
| MCF-10-2A | 633 | ++ | + |
| | 911 | ++ | + |
| MCF-10-2F | 633 | ++ | ++ |
| | 911 | ++ | ++ |
| MCF-12M | 1493 | ++ | ++ |
| | 1663 | + | ± |
| MCF-12A | 1952 | − | −* |
| MCF-12F | 1952 | − | −* |

N.D., no data; cells were not available for assay due to low proliferation of MCF-10M[661] in low calcium, serum-free medium.
* Predominant cell type.
++ Heterogeneous staining, greater than 50% of the cells stained.
+ Heterogeneous staining, less than 50% of the cells stained.
± Staining in very few cells (<1%).
− No staining.

The cytokeratin expression clearly shows that the immortal cell lines of MCF-10-2A and MCF-10-2F are distinct from the immortal cell lines of U.S. Pat. No. 5,026,637.

As noted above, cell line MCF-10-2 of the present invention and MCF-10 of U.S. Pat. No. 5,026,637 have common lineage. For convenience, Table 3 below provides the distinguishing characteristics of the two cell lines (i.e., the differences between MCF-10-2 and MCF-10).

TABLE 3

| Characteristic | MCF-10 | MCF-10-2 |
|---|---|---|
| Lineage | MCF-10M[661], continuously cultivated | MCF-10M[341], reactivated after cryopreservation |
| Karyotype | near diploid (46–48 chromosomes) | hypodiploid (40–43 chromosomes) |
| Doubling Time (subline A; hrs) | 19.9 | 21.4 |
| Saturation Density (subline A; cell/cm$^2$) | 2.5 × 10$^4$ | 1.6 × 10$^4$ |
| Dome Formation | many domes in pre-confluent monolayers | few domes, only in post-confluent monolayers |
| Epithelial Cytokeratins | no expression of cytokeratin 19 | expression of cytokeratin 19 |

Based on this data, it is clear that cell lines MCF-10-2 of the present invention and MCF-10 of U.S. Pat. No. 5,026,637 are different and distinct cell lines in spite of their common lineage.

In addition to the novel cell lines of the present invention, the present invention provides a method for testing the effect of long-term exposure of epithelial cells in culture to a preselected agent. Accordingly, a culture of MCF-10-2A or MCF-10-2F would be exposed to a preselected agent, such as a suspected carcinogen. The cells would then be observed over an extended period of time to determine the effects, if any, of the exposure. In this manner, long-term studies of epithelial cells can be performed which were not previously possible.

In addition, the present invention could provide a method for producing proteins from human mammary epithelial cells which comprises the steps of culturing MCF-10-2A or MCF-10-2F and collecting proteins produced by the cells. The separation and isolation of proteins from somatic cells is well known in the art and suitable methods will be apparent.

The present invention has been described in connection with specific embodiments thereof; however, as will be appreciated by those skilled in the art, many modifications may be made to the invention without departing from the spirit and scope of the claims herein.

What is claimed is:

1. A biologically pure culture of an immortal human mammary epithelial cell subline designated Registration No. ATCC CRL 10781.

2. A biologically pure culture of an immortal human mammary epithelial cell subline designated Registration No. ATCC CRL 10780.

3. A cell culture containing cells from a biologically pure culture of an immortal human mammary epithelial cell subline designated Registration No. ATCC CRL 10781.

4. A cell culture containing cells from a biologically pure culture of an immortal human mammary epithelial cell subline designated Registration No. ATCC CRL 10780.

* * * * *